US010927404B1

(12) United States Patent
Khalid et al.

(10) Patent No.: US 10,927,404 B1
(45) Date of Patent: Feb. 23, 2021

(54) PATHOGEN DETECTION USING APTAMER MOLECULAR BEACONS USING A MOBILE DEVICE

(71) Applicant: 4233999 Canada Inc., Westmount (CA)

(72) Inventors: Najeeb Ashraf Khalid, Westmount (CA); Naqeeb Khalid, Brampton (CA)

(73) Assignee: 4233999 CANADA INC., Westmount (CA)

( * ) Notice: Subject to any disclaimer, the term of this patent is extended or adjusted under 35 U.S.C. 154(b) by 0 days.

(21) Appl. No.: 17/026,138

(22) Filed: Sep. 18, 2020

Related U.S. Application Data

(60) Provisional application No. 63/044,602, filed on Jun. 26, 2020.

(51) Int. Cl.

| | |
|---|---|
| ***G06K 9/00*** | (2006.01) |
| ***H04N 9/47*** | (2006.01) |
| ***C12Q 1/6823*** | (2018.01) |
| ***G06T 7/00*** | (2017.01) |
| ***G06K 7/14*** | (2006.01) |
| ***G06K 9/20*** | (2006.01) |

(52) U.S. Cl.
CPC ......... *C12Q 1/6823* (2013.01); *G06K 7/1413* (2013.01); *G06K 9/00134* (2013.01); *G06K 9/2027* (2013.01); *G06T 7/0012* (2013.01); *G06T 2207/30024* (2013.01)

(58) Field of Classification Search
USPC ....... 382/100, 103, 128–134, 162, 168, 173, 382/181, 209, 224, 254, 321; 345/14; 348/63, 68, 77, 79, 236
See application file for complete search history.

(56) References Cited

U.S. PATENT DOCUMENTS

| | | | | |
|---|---|---|---|---|
| 2010/0216175 | A1* | 8/2010 | Melker | A61B 5/1486 435/14 |
| 2016/0231324 | A1* | 8/2016 | Zhao | G01N 33/54366 |
| 2016/0274105 | A1* | 9/2016 | Whitesides | G01N 33/526 |
| 2017/0316487 | A1* | 11/2017 | Mazed | B82Y 5/00 |
| 2017/0370836 | A1* | 12/2017 | Gerion | G01N 21/253 |
| 2019/0079063 | A1* | 3/2019 | Gilboa-Geffen | G01N 1/08 |
| 2020/0283843 | A1* | 9/2020 | Regev | C12N 15/1075 |

OTHER PUBLICATIONS

Xiaodan Zeng; Wen Yang; Fluorescence detection of adenosine triphosphate through an aptamer-molecular beacon multiple probe; Publication Aug. 11, 2112.*

* cited by examiner

*Primary Examiner* — Seyed H Azarian
(74) *Attorney, Agent, or Firm* — Anglehart et al.

(57) ABSTRACT

This disclosure pertains to a testing method for a target pathogen. The method uses biosensors with particular fluorescence characteristics, such that when the biosensor binds to a target pathogen, a fluorophore may emit light if excited. The biosensor may be an aptamer-based biosensor with a fluorophore reporter and a quencher. The excitation of the fluorophore and the detection of fluorescence may be made through the use of a flashlight source and a camera from a mobile device, such as a smartphone.

13 Claims, 7 Drawing Sheets

79 Start mobile device testing application
81 Scan vial barcode
83 Add sample saliva or nasal mucus in vial
85 Shake vial
87 Insert vial in testing device fixture
89 Insert mobile device in testing device fixture
91 Perform test
93 Display test results

PATHOGEN DETECTION USING APTAMER MOLECULAR BEACONS USING A MOBILE DEVICE

CROSS-REFERENCE TO RELATED APPLICATIONS

The present patent application claims priority of U.S. provisional patent application Ser. No. 63/044,602 filed on 26 Jun. 2020.

TECHNICAL FIELD

The field of this invention is the detection of pathogens using aptamers, particularly by using Aptamer Molecular Beacons (AMB) and a camera-equipped device, such as a mobile device, smartphone or equivalent.

BACKGROUND

Aptamers are oligonucleotide or peptide molecules that bind to a specific target molecule and that have been studied as early as 1990. Aptamer-based biosensors have been developed for use in a wide variety of sensing technique, such as electrochemical, optical and mass-sensitive analytical techniques. Aptamers exhibit many advantages as recognition elements in biosensing when compared to traditional antibodies. They are small, chemically stable and cost effective. More importantly, aptamers offer remarkable flexibility and convenience in the design of their structures, which has led to novel biosensors that have exhibited high sensitivity and selectivity.

Aptamers are well known to have distinctly different conformations and structures before and after binding with the targets. In fluorophore-based aptamers, the structural changes of aptamer may modify the structure such that a quencher-reporter structure (i.e. an aptamer molecular beacon) may be separated, thus allowing the reporter to exhibit fluorescence when excited with a light source at a certain wavelength.

Aptamers may be developed and selected specifically for a target pathogen and therefore may be used in diagnostic tests for almost any infection. The fluorescence produced by an aptamer molecular fluorescence beacon is generally detected through fluorescence spectroscopy or fluorometry, which are costly equipment which are not necessarily portable. Additionally, the complexity of operations of such equipment is inherently high and require specific training. Therefore, aptamer-based testing is not accessible for most applications and may not be used in most facilities.

Since aptamers may be developed for a specific pathogen, its diagnostic testing capabilities are incredible, but the current limitations for analyzing the aptamer's response do not allow for its widespread use. As such, it would be beneficial to have an aptamer-based testing device which may be affordable, operable by almost anyone and with no highly specialized devices (other than the aptamer filled testing vial). A portable testing unit may further be desirable as it may allow testing anywhere.

SUMMARY

Applicant has discovered a testing method for a target pathogen that may be used with a mobile device, such as a smartphone, instead of specialized devices. By selecting an Aptamer that binds uniquely to the virus that is the target for a test, and by attaching a selected appropriate fluorophore and matching quencher for the chosen aptamer, an Aptamer Molecular Beacon may be formed. This Aptamer Molecular Beacon displays the property that prior to binding to the specific virus, it has a shape where the quencher is in proximity to the fluorophore, and when it binds, the shape changes and the quencher molecule separates from the fluorophore. The fluorophore then, on receiving incident light will fluoresce at a different wavelength than the incident light. The aptamer, the fluorophore and the quencher can be specifically selected to have an excitation wavelength that approximately is the same as a smartphone LED's spectral peak and the emitted light can be within the range of sensitivity of the smartphone's camera sensors.

As a matter of fact, most mobile devices use the same type of LED flash technology which produces white light by using a blue GaN light-emitting diode (LED) (e.g. emitting with a peak at about 460 nm) with a layer of light-emitting phosphor to produce other wavelengths so that the combination of wavelengths appears to be white to the human eye. This white LED output contains a reasonably narrowband source of optical power in the blue part of the spectrum A first broad aspect is an aptamer molecular beacon testing device for detecting a pathogen including: a receptacle for receiving a test vial; a coupler for receiving a mobile device having a camera and a flash light source, the coupler being positioned with respect to the receptacle to allow for light from the flash light source to reach the test vial and for fluorescence light from the test vial generated in response to the light from the flash light source to reach the camera; and a lightproof enclosure for preventing external ambient light from reaching the camera when the mobile device is coupled.

In some embodiments, the aptamer molecular beacon testing device further includes a bandpass optical filter to allow the light from the flash light source to reach the Aptamer Molecular Beacon while allowing the fluorescence from the fluorophore bound to the aptamer to reach the camera.

In some embodiments, the mobile device and the test vial are completely enclosed in the lightproof enclosure.

In some embodiments, the coupler is a slot in the lightproof enclosure.

In some embodiments, the coupler includes an opaque seal.

In some embodiments, the lightproof enclosure further includes a movable gate to access the test vial receptacle, the movable gate being configured to prevent the ambient light from leaking inside the lightproof enclosure in a closed position.

In some embodiments, the coupler is one of a mobile device cover or an attachable mobile camera cover.

In some embodiments, the aptamer molecular beacon testing device further includes a reference element operable to emit light in response to receiving a light excitation.

In some embodiments, the test vial receptacle further includes a movable part operable to displace the reference element from a rest position to a deployed position when a replaceable test vial is fully inserted in the test vial receptacle, the reference element being outside a field-of-view of the camera in the rest position and inside the field-of-view in the deployed position.

In some embodiments, the aptamer molecular beacon testing device further includes at least one of a mobile device adapter and an aperture selector configured to adapt the lightproof enclosure to different mobile devices.

In some embodiments, the bandpass optical filter includes a gap configured to allow any light source through.

A second broad aspect is an aptamer molecular beacon testing device for detecting a pathogen including: a lightproof enclosure configured to receive a test vial, the lightproof enclosure including at least a light source and a camera cell.

In some embodiments, the aptamer molecular beacon testing device further includes a communication module operable to transmit information to a computing device and receive information from the computing device.

In some embodiments, the aptamer molecular beacon testing device further includes a battery providing power to at least the light source and the camera cell.

A third broad aspect is a pathogen testing system including: an aptamer molecular beacon testing device; and a replaceable aptamer molecular beacon test vial configured to be placed in the test vial receptacle, the replaceable aptamer molecular beacon test vial having a body being configured to receive a sample fluid from a tested subject, the test vial body including a solution of aptamer molecular beacons and a carrier liquid medium, wherein the aptamer molecular beacons are selected to bind to a protein, RNA or DNA of a target pathogen and further include a reporter molecule that is capable of receiving light and emitting light after binding to the target pathogen.

In some embodiments, the lightproof enclosure is configured to position the mobile device and the replaceable aptamer molecular beacon test vial such that a light from the flash light source illuminates the replaceable aptamer molecular beacon test vial and such that the camera is operable to capture the emitted light from the Aptamer Molecular Beacons.

In some embodiments, the reporter molecule emits light at a wavelength which corresponds to a peak sensitivity of at least one light sensor of the mobile device.

In some embodiments, an optical filter is configured to cover a lens of the camera while leaving the flash light source uncovered to limit a light received by the camera to a wavelength corresponding to an emission wavelength of the reporter molecule. In such a case, simultaneous excitation of the fluorophore and detection of the emission light can be possible. This is useful when the lifetime of the fluorescence is very short. This can also be useful for eliminating background light when ambient light is otherwise able to reach the camera.

In some embodiments, the replaceable aptamer molecular beacon test vial includes an opaque seal surrounding a removable cap configured to be attached to the test vial.

In some embodiments, the replaceable aptamer molecular beacon test vial is a test slat, the container being a top surface of the test slat.

In some embodiments, the pathogen testing system further includes a reflective sticker over a surface of the container.

In some embodiments, the reflective sticker includes a barcode.

A fourth broad aspect is a pathogen testing aptamer molecular beacon test vial configured to be placed over a camera and a flash light source of a mobile device, including a molecular beacon aptamer test solution, wherein the Aptamer Molecular Beacons are selected to bind to a protein, RNA or DNA of a target pathogen and further include a reporter molecule that is capable of receiving light and emitting light after binding to the target pathogen, a reflective or opaque material covering a surface of the test vial and having a first window for placement over the flash light source of the mobile device camera and a second window for placement over a lens of the camera of the mobile device, the second window having a bandpass optical filter area for absorbing at least the light from the flash light source while allowing the fluorescence light to reach the camera.

In some embodiments, the vial includes a lid covering a fluid chamber.

A fifth broad aspect is a mobile device readable non-transitory memory storing instructions executable by a mobile device, including: at least one instruction for causing a flash module of the mobile device to be operated; at least one instruction for at least one camera of the mobile device to capture an image of a vial including a solution of a test subject fluid, a quantity of Aptamer Molecular Beacons and a carrier liquid medium; at least one instruction for a processor of the mobile device to compute an infection status based on the captured image; and at least one instruction for the processor to display the infection status on a display module of the mobile device.

In some embodiments, the memory further includes at least one instruction for causing operation of the flash module to be stopped before executing the at least one instruction for at least one camera of the mobile device to capture an image.

In some embodiments, the memory further includes at least one instruction for storing at least one of the captured image and the infection status in a storage module of the mobile device.

In some embodiments, the memory further includes at least one instruction for sending at least one of the captured image and the infection status to a remote server.

In some embodiments, the memory further includes at least one instruction to scan a barcode or receive a code associated with the vial and to determine at least one of the state of a replaceable test vial and a target pathogen being tested.

In some embodiments, the memory further includes at least one instruction to prevent the mobile device from being operable to determine infection status when the state of the replaceable test vial indicates an invalid replaceable test vial.

In some embodiments, the memory further includes at least one instruction to confirm at least one of a presence of the replaceable test vial and a negative infection status test result by processing the captured image and identifying a reference element.

A sixth broad aspect is a method for detecting a pathogen including: starting a mobile device software testing application; adding a test subject sample fluid to a replaceable aptamer molecular beacon test vial including a solution of Aptamer Molecular Beacons and a carrier liquid medium, wherein the Aptamer Molecular Beacons are selected to bind to a protein, RNA or DNA of a target pathogen and further include a reporter molecule that is capable of receiving light and emitting light after binding to the target pathogen; mixing a content of the replaceable aptamer molecular beacon test vial; aligning the aptamer molecular beacon test vial with a camera and a flash light source of the mobile device; and performing a test to detect a presence of the target pathogen by running the mobile device software testing application.

In some embodiments, the performing the test includes causing the flash light source to be operated and the camera to capture an image of the replaceable aptamer molecular beacon test vial.

In some embodiments, the method further includes at least one of computing an infection status based on the captured image and displaying the infection status on a display of the mobile device.

In some embodiments, the method further includes storing at least one of the captured image and an infection status in a storage module of the mobile device.

In some embodiments, the method further includes sending at least one of the captured image and the infection status to a remote server.

In some embodiments, the method further includes scanning a barcode with the mobile device to determine at least one of the states of a replaceable test vial and a target pathogen being tested.

In some embodiments, the method further includes preventing the mobile device from being operable to determine infection status when the state of the replaceable test vial indicates an invalid replaceable test vial.

In some embodiments, the method further includes confirming at least one of a presence of the replaceable test vial and a negative infection status test result by processing the captured image and identifying a reference element.

BRIEF DESCRIPTION OF THE DRAWINGS

The invention will be better understood by way of the following detailed description of embodiments of the invention with reference to the appended drawings, in which:

FIGS. 4A-4B are schematic drawings of an exemplary aptamer molecular beacon testing device fixed to a mobile device;

DETAILED DESCRIPTION

Recent advances in bioscience have made it possible to detect pathogens without the complex methods being employed up to now. These Aptamers Molecular Beacons bind to specific pathogens that can in turn emit light when being bound to the target pathogen. Devices such as smartphones have the computing means to analyze the results and provide the conclusion, and store the results locally or communicate them, if so desired.

Aptamers

Aptamers are single stranded nucleic acid molecules or peptide molecules that fold into complex three-dimensional conformations that can selectively bind to a specific target, including proteins, peptides, carbohydrates, small molecules, toxins, and even live cells. Aptamers assume a variety of shapes due to their tendency to form helices and single-stranded loops. Aptamers can be developed to bind to any desired target. The aptamer can be generated via in-vitro selection or via SELEX (systematic evolution of ligands by exponential enrichment) ranging from metal ions to cells. On the molecular level, the aptamers will bind to its cognate target by non-covalent interactions. As such, aptamers may be specifically designed to bind to any pathogens (e.g. viruses, bacteria, spores, etc.) to help in diagnosis or to deliver drugs to specific cells inside a patient. One such aptamer has been proven to bind to SARS-CoV-2 S1 spike protein on the surface of the virus. Other Aptamers can be chosen or designed to bind to other proteins or RNA or DNA of other viruses and pathogens.

Fluorophores

Fluorophores are molecules that can be very small, <1200 Daltons that may be attached to one end of the aptamer. One such fluorophore that exhibits the desired properties that match the characteristics of the smartphone LED and cameras is Atto 465 (e.g. from Sigma Aldrich). As described herein, the fluorophore may be used as the reporter in an Aptamer Molecular Beacon.

Quencher

A quencher is also a small molecule that can be attached to the opposite end of the aptamer than the fluorophore. The quencher, while in proximity with the fluorophore, absorbs the energy from the fluorophore that would otherwise be emitted. On separation from the fluorophore, the quencher stops being operable to absorb this energy, therefore allowing the fluorophore to emit light. This separation occurs, in an appropriately designed aptamer, on binding to the target protein, RNA or DNA. One quencher that will attach and quench the Atto 465 fluorophore is the Iowa Black® Fluorescence Quencher.

Aptamer Molecular Beacons (AMB)

Figure 1:
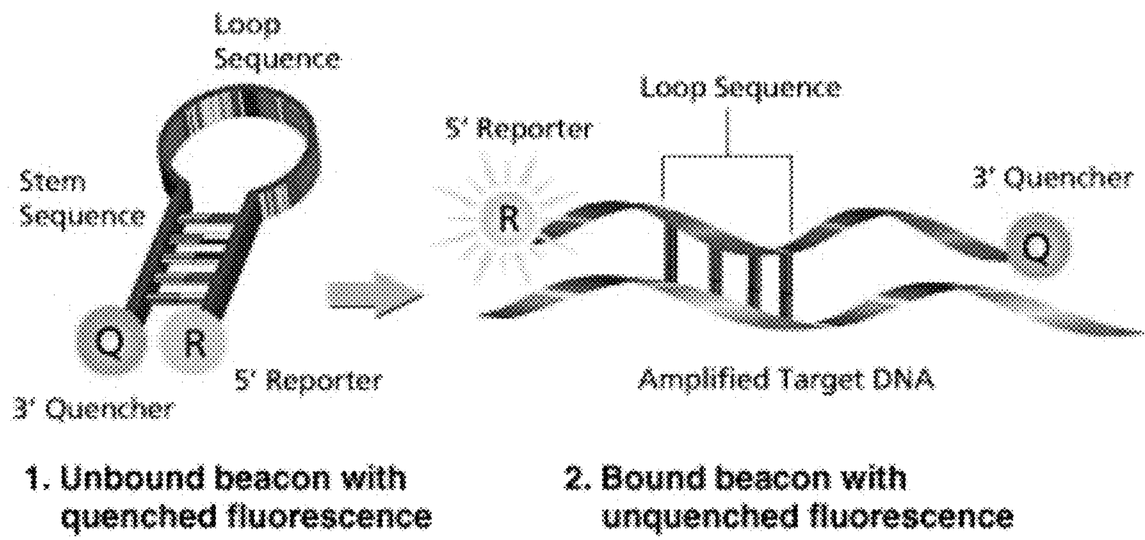
FIG. 1 is a composite illustration of a fluorescence Aptamer Molecular Beacon in a folded and attached position, as found in the prior art.

As illustrated in FIG. 1, a Molecular Beacon may be an aptamer with the fluorophore, which is the AMB reporter, and quencher attached at the two end of the aptamer held in a hairpin-loop conformation (around 20 to 25 nucleotides) by complementary stem sequences (around 4 to 6 nt) at both ends of the probe. The 5' and 3' ends of the probe contain a reporter and a quencher molecule, respectively. The loop may be a single-stranded sequence complementary to the target sequence. The proximity of the reporter and Quencher causes the quenching of the natural fluorescence emission of the reporter.

Aptamer Molecular Beacons hybridize to their specific target sequence causing the hairpin-loop structure to open and separate the reporter and the quencher. As the Quencher is no longer in proximity to the reporter, fluorescence emission may take place when the necessary excitation is provided to the molecule. Therefore, the measured fluorescence signal may be directly proportional to the amount of target pathogen. As a matter of fact, the more testing solution contains the target pathogen, the more Aptamer Molecular Beacons will be attached and have their reporter separated from their quencher (i.e. the fluorescence signal will be stronger). There are different 3D shapes and changes to the morphology of the Aptamer Molecular Beacons on binding to follow the change on binding. Similarly, the fluorophore and quencher conjugation to the aptamer may be different. In some cases, the quencher can be released.

As is known in the art, the fluorophore may be selected to emit light for a particular wavelength of absorbed light.

Aptamer Molecular Beacon (AMB) Testing Device

As described herein, the Applicant has discovered a method of testing for a pathogen using a mobile device and an Aptamer Molecular Beacon solution. As a matter of fact, it is possible to select an AMB with a fluorophore excitable by the main wavelength of the light emitted by a mobile device's flash. Given the optical properties of most cameras included in current mobile devices, the camera may be operable to detect fluorescence emitted by AMBs bound to target pathogens. In order to detect low levels of emitted fluorescence, a bandpass filter may be required. The filter may thus allow the mobile device's camera to sense a small amount of the target pathogen, such as would be present in a patient in early stages of infection while further filtering out fluorescence from water in the solution and other contaminants in the saliva such as food particles and fruit particles.

In some embodiments, the bandpass filter may not be required for the system to properly function. As such, the bandpass filter may not be required when a sufficiently lightproof enclosure (i.e. no leakage of ambient light) and a fluorophore operable to emit light for a long enough period after the excitation light source has stopped are used. As a matter of fact, these may allow the testing device to flash the light source and to capture an image after the light source has been extinguished (i.e. the only light being captured would be the light emitted by the fluorophores, therefore no filter may be required).

In some embodiments, there AMB may be selected to bind with a given surface protein of the severe acute respiratory syndrome coronavirus 2 (SARS-CoV-2, the virus causing COVID-19) and where the quencher and the reporter are chosen to be excited by a light source having approximately 450 nm and emit at 490 nm, or appreciably similar wavelength. Someone skilled in the art will appreciate the fact that the AMB may be selected to bind to any pathogen.

In order to perform a diagnostic test to determine the infectious state of a person with regards to a target pathogen, a sample of the saliva or nasal mucus may be taken with a swab and inserted into a vial. The vial contains the AMB and a carrier liquid medium, such that when the vial is shaken the person's saliva or nasal mucus may mix with the AMB and carrier liquid medium.

Figure 2:
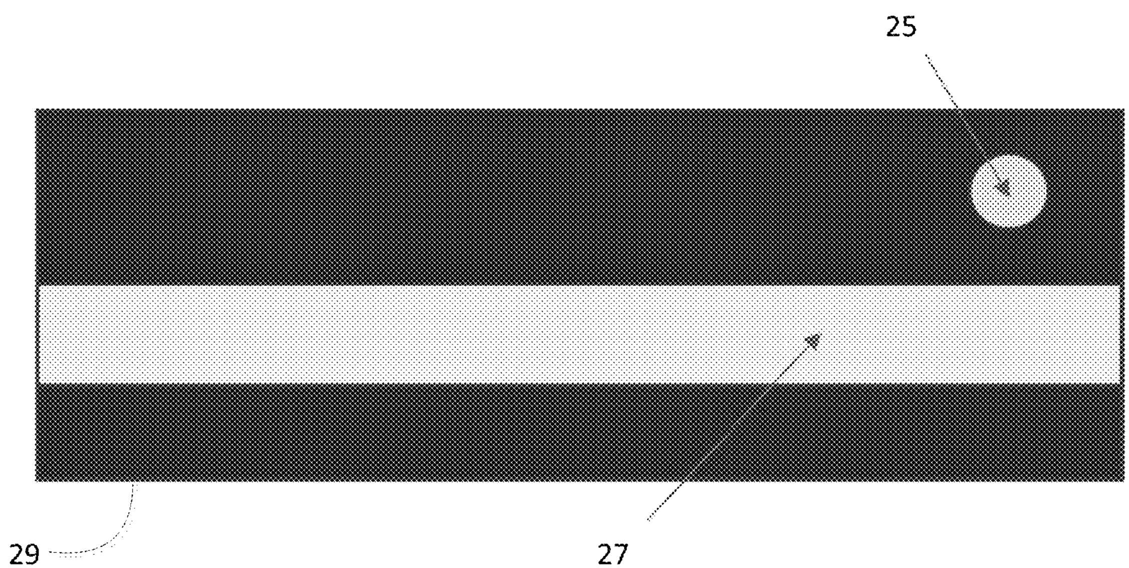
FIG. 2 is a schematic of an exemplary aptamer molecular beacon testing device for a mobile device.

Reference is now made to FIG. 2, which is a schematic of an exemplary aptamer molecular beacon testing device for a mobile device. In this embodiment, a fixture 29, which may be a lightproof enclosure, contains a slot for a mobile device 27 (e.g. smartphone, tablet, etc.) and a receptacle for a test vial 25. The receptacle for the test vial 25 may be a slot and may be positioned inside the fixture 29 such that the distance from the vial to the flash of the smartphone and the distance between the vial and the camera lens selected to gather the light emitted by the reporter is constant within a small covariance. This ensures that the Beer-Lambert law calculations in the mobile device application may be respected. Someone skilled in the art will appreciate that, as such, the extinction ratio of the medium is known, the distance from the flash is known and the light flux is known.

In some embodiments, the slot for the mobile device 27 may be a coupler which effectively joins the mobile device to the fixture 29. For example, a relatively small fixture 29 may be positioned over a mobile device, such that it only covers an area over a camera and a flash of the mobile device. In such example, the slot for the mobile device 27 may be replaced by the connection between the mobile device and the fixture 29, which is herein defined as a coupler. The coupler may be lightproof, such that no ambient light may leak to the inside of the enclosure/fixture 29. In some embodiments, the coupler may be a mobile device cover that fits over the mobile device and holds the other parts of the testing device in the required position over the flash and camera(s).

Figure 3A:
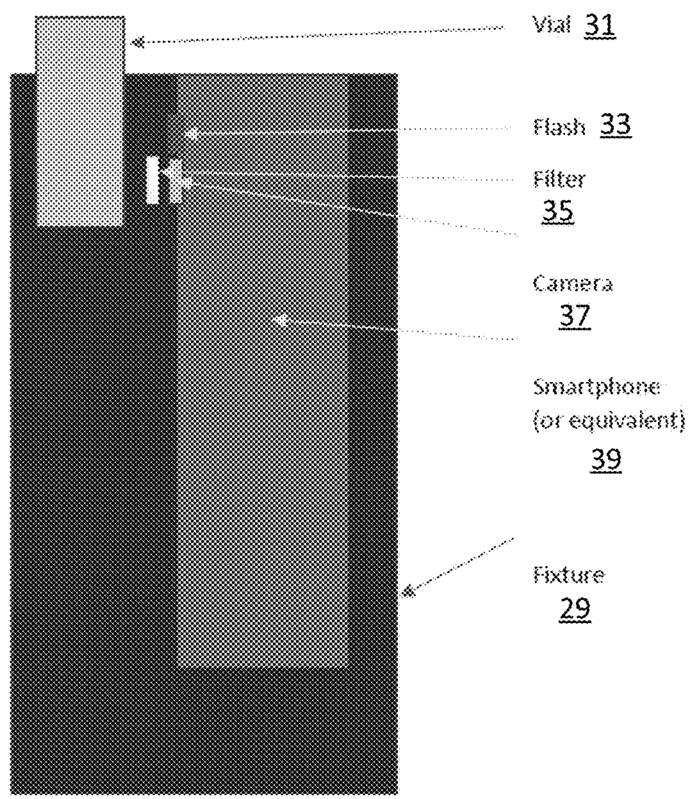
FIG. 3A is a schematic illustrating some internal components of an exemplary aptamer molecular beacon testing device for a mobile device.

FIG. 3A illustrates internal components of an exemplary aptamer molecular beacon testing device for a mobile device. In this embodiment, a mobile device 39 (e.g. smartphone, tablet, etc.) may be inserted inside the fixture's 29 slot for the mobile device. As the mobile device 39 is positioned correctly inside the slot, its flash 33 and camera 37 may be aligned with their associated apertures in the fixture 29 and thereafter also aligned with the test vial 31. The test vial 31 may be inserted in the fixture's 29 slot for the test vial, such that the vial is correctly positioned to allow its content to be illuminated by the flash 33 and for its potential fluorescence to be detected by the camera 37.

The mobile device's 39 camera 37 may be aligned with a filter 35, which may be a notch optical filter specific to 490 nm (e.g. a bandpass filter with a narrow band around 490 nm). As the mobile device's 39 may have a flash 33 made of Light Emitting Diodes that have a fundamental light emission between 450 to 460 nm, the fluorophore may emit light at around 490 nm such that it may be the only light to pass-through the filter 35. In some embodiments, the optical filter may include a small gap to allow any light to pass-through, such that an aligned camera may sense the intensity of flash and may be able to confirm the presence of a vial inserted in the vial's receptacle. In some embodiments where the filter is not required, as described herein, the detection of the vial may be done by capturing a first image of the vial while the light source is operating. The testing may subsequently be done by operating once more the light source and thereafter capturing an image once the light source has extinguished (such that only a presence of fluorophores may be emitting). Someone skilled in the art will appreciate that it may be feasible to continuously capture a series of image, some of them being while the light source is operating (i.e. confirming the presence of the vial) and some of them after the light source has extinguished.

The reporter quantum efficiency and the absorbance of the light by the liquid medium will determine the light emission quantity in number of photons. As mobile devices 39 have different of cameras and that some mobile devices may have multiple camera sensors, the testing system, through the control application, may select the camera lens with the highest quantum efficiency for the testing, this being about 75% at 490 nm. Additionally, any image processing capabilities of smartphones or other mobile devices may be used to enhance the image captured during the test. These capabilities may include post-processing software, which may include artificial intelligence image processing. This may enhance the sensitivity of the test and therefore allow for detection of the target pathogen in relatively small quantities.

The sensors in the smartphone or similar device can use a single cell of the camera sensor or a plurality, or all, the cells of the sensor to calculate the results of the test performed. This maybe done immediately as part of the test process or stored over time and multiple tests and then analyzed. The fluorophore emission light can be taken from a specific region of interest within the acquired image. Spatial intensity analysis can be used to confirm that the intensity observed matches intensity from the expected distribution of the aptamer within the solution of the vial.

It will be appreciated that the test result can apply a simple threshold to the total amount of light observed to give essentially a binary result, or the amount of light received can be used to qualify or quantify the result. This can allow the positive or negative result to be qualified with a confidence value that health care professionals can consult. In some tests, the amount of light in the acquired image can be used to be correlated with a disease state or disease severity.

The fluorophore can have a lifetime that will permit the emission light to be captured by the mobile device's camera once the flash light source is turned off.

A reflector may further be placed behind the vial to reflect any light emitted by the fluorophore back to the camera, similarly a tube can be placed between the vial and the camera to eliminate any external light from effecting the reading. A similar absence of ambient or external light maybe achieved by another means as well.

Figure 3B:
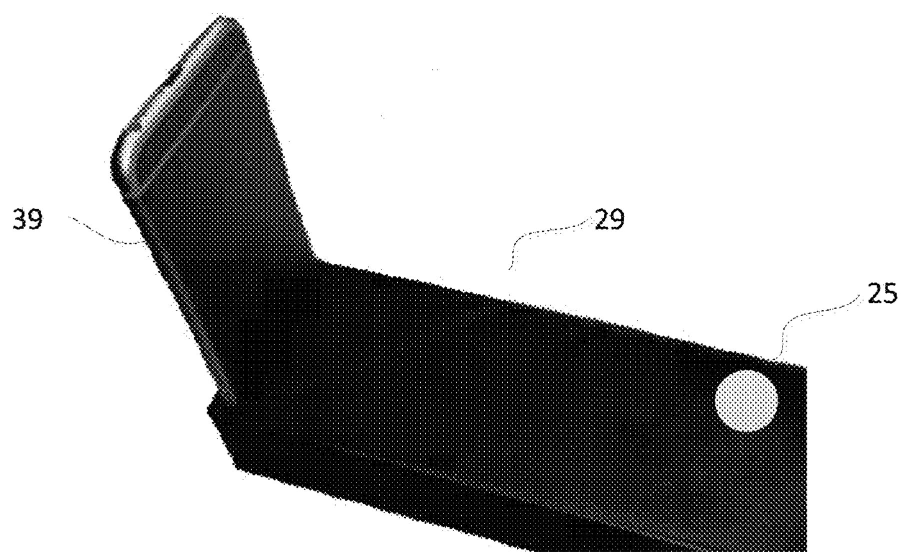
FIG. 3B is an illustration of an exemplary aptamer molecular beacon testing device setup comprising a mobile device inserted in the enclosure.

FIG. 3B illustrates an exemplary aptamer molecular beacon testing device setup comprising a mobile device 39 inserted in the enclosure. In this embodiment, the fixture 29 may have a long form factor such that the testing device may be placed on a mostly horizontal surface (e.g. a table, counter, desk, etc.) without tilting over or moving throughout the test. As a matter of fact, a smaller form factor may be prone to tilting or moving once the mobile device 39 is inserted at one end of the device. It will be appreciated that any different form factor may be used for the testing device as it may be specified to hold the device throughout the test in the accompanying testing method description.

In the embodiment of FIG. 3B, a test vial slot 25 in the fixture 29 is included on the opposite side of the mobile device's 39 slot. The test vial slot 25 may be aligned with the mobile device's 39 camera(s) and flash. As such, the test vial slot 25 may be positioned differently depending on the model of mobile device 39 to be used in the testing device. The test vial slot 25 may be a cavity which may be completely covered by an opaque vial cap, such that no ambient light may enter inside the fixture's 29 testing chamber.

Figure 3C:
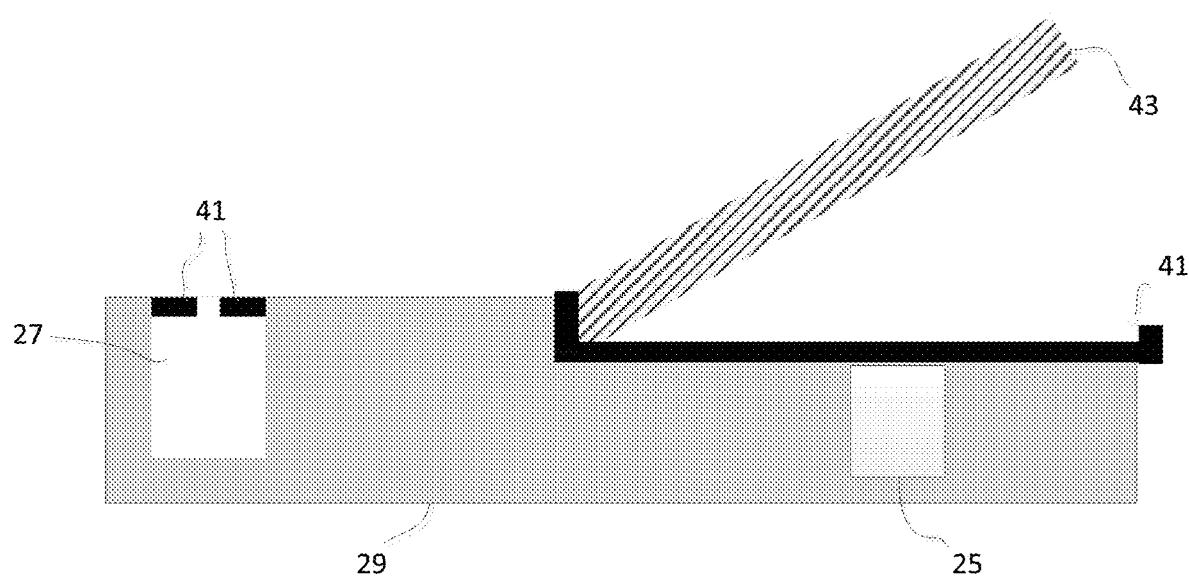
FIG. 3C is a schematic of an exemplary aptamer molecular beacon testing device with a gated access to the sample enclosure.

FIG. 3C is a schematic of an exemplary aptamer molecular beacon testing device with a gated access to the sample enclosure. In this embodiment, the mobile device slot 27 may have an opaque seal 41 enclosing its opening in the fixture 29, such that no ambient light may leak through the opening into the testing chamber. Ambient light leakage may otherwise impact the mobile device's camera(s) sensors to a point where their sensibility to the fluorescent light that may be emitted by a tested sample in a test vial is detrimentally affected.

In the embodiment of FIG. 3C, there may be a gate 43 providing an easy access to the test vial slot 25. Similar to the opaque seal 41 surrounding the mobile device slot 27, an opaque seal 41 may surround the gated access point. As such, when the gate 43 is closed and pressed against the fixture 29, the opaque seal 41 may prevent any ambient light from leaking inside the testing device.

Figure 3D:
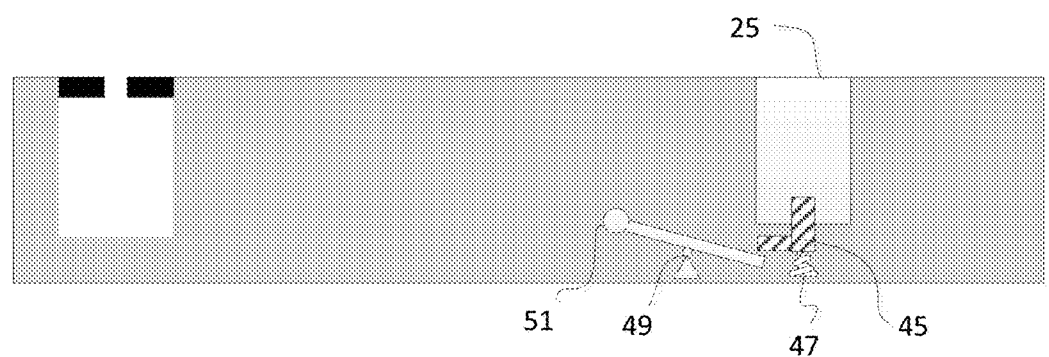
FIG. 3D is a schematic of an exemplary aptamer molecular beacon testing device with a sample engagement and reference unit.

Now referring to FIG. 3D, which is a schematic of an exemplary aptamer molecular beacon testing device with a sample engagement and reference unit. In some embodiments, it may be desirable to include a system that may indicate whether the test vial is correctly and completely inserted inside the test vial slot 25. This may be necessary to ensure that an opaque seal is properly formed by a test vial cap (i.e. no ambient light may leak and impact test results) or that all of the part in which the vial is filled by the mix of AMB, carrier liquid medium and sample from the test subject is exposed to the light source (e.g. flash). Additionally, this system may be used as a reference point to calibrate the mobile device's camera(s) and/or to show that a negative test has been successfully completed and is not the result of an error or malfunction.

For example, FIG. 3D illustrates a mechanical engagement and reference system in which the complete insertion of a test vial inside the test vial slot 25 pushes an engagement member 45 towards a bottom of the fixture 29. The engagement member 45 may thereafter push a rotary member 49 on which is fixed a fluorescent part 51. The engagement member 45 may be connected to a biasing member 47 (e.g. a compression spring) which may reset the engagement and reference system to a resting position once a test vial is removed from the test vial slot 25.

In its resting position, the fluorescent part 51 of the engagement and reference system may be outside of the field-of-view of the mobile device's camera(s). When a test vial is fully engaged and the engagement and reference system is in its deployed position, the fluorescent part 51 may be inside the field-of-view (FoV) of the mobile device's camera(s). The deployed position of the engagement and reference system may be positioned such that it does not interfere with the detection of AMBs from the test vial while remaining inside the FoV of the camera(s). This may be particularly useful to ensure that no malfunction happened during a test, mostly for a negative test result.

As a matter of fact, a negative test result necessarily means that no AMBs emitted light, or that an insignificant number of AMBs emitted light. Thus, a negative result for a test may be the detection of a completely dark testing chamber inside the testing device. Some device or mobile device application failures or malfunction may lead to similar results, such as the non-operation of the flash, an issue with the flash and/or camera controls, etc. This may mean that a false-negative result may be given to the person being tested, potentially leading to the person unknowingly spreading the disease.

When equipped with an engagement and reference system such as the one described herein, the fluorescent part 51 may be present in the sensed picture. Thus, while there may be no light emitted from the test vial (i.e. negative test result), the test may be confirmed as having successfully taken place by the recording of the fluorescent part 51 being in the FoV.

Someone skilled in the art will appreciate that any other configuration of an engagement and reference system may be used without departing from the teachings of this disclosure. Systems may also be used for only one of the functions of the described engagement and reference system (e.g. only for engagement of the vial or only for the reference). As such, other mechanical configurations or other systems (e.g. electrical, magnetic, etc.) may be used in lieu of the one described herein. Optical engagement and reference system may use other light sources (e.g. phosphorescent). A static reference system may be used, in which a fluorescent part 51 or equivalent is fixed at the "deployed" position (i.e. always in the FoV of the camera(s)).

Figure 3E:
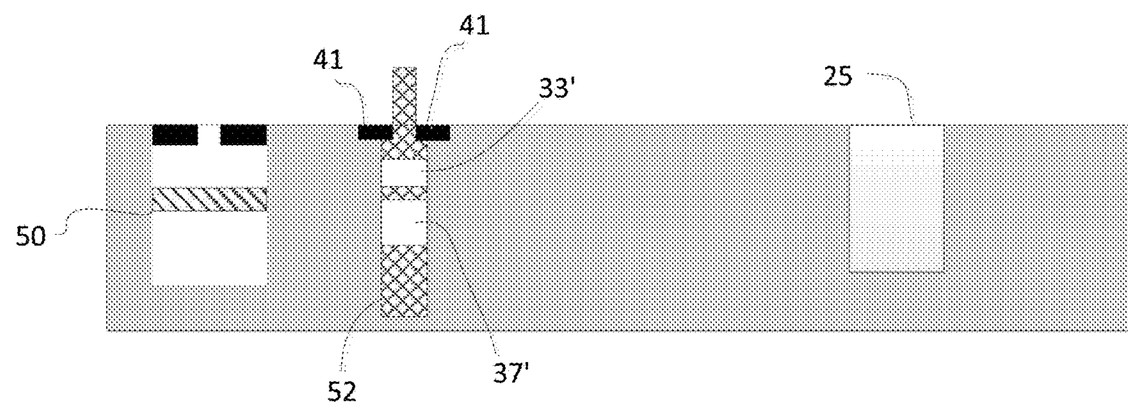
FIG. 3E is a schematic of an exemplary aptamer molecular beacon testing device with a removable flash and camera apertures part.

Now referring to FIG. 3E, which is a schematic of an exemplary aptamer molecular beacon testing device with a removable flash and camera apertures part 52. As there are a significant number of mobile devices on the market, it may be desirable to have a modular AMB testing device fixture 29 design. The mobile device slot may be adapted to fit most smartphones (most tablets in a bigger fixture, etc.). In order to ensure the position of the mobile device inside the slot, such that the flash and camera are correctly positioned and do not move during the test, the device may include a replaceable mobile device adapter 50 configured to fit around the mobile device and resting on the sides of the mobile device slot. The testing device may thus have a mobile device adapter 50 specific for the mobile device being used for the test.

Similarly, as the size and the positioning of the flash and camera(s) differs between mobile device models (and its position inside the mobile device slot), a replaceable aperture selector 52 may be inserted in the fixture 29 in an aperture selector slot that may be positioned between the mobile device slot and the test vial slot 25. The aperture selector 52 may include the necessary flash aperture 33' and the one or more camera apertures 37' that are associated with the mobile device to be used and inserted inside the mobile device slot. Additionally, the opening of the aperture selector slot on the fixture 29 may include an opaque seal surrounding the area.

Using different mobile device adapters 50 and their associated aperture selector 52 may allow the user of the testing system to operate it with multiple different devices. This may be particularly useful for businesses in which different operators may perform the tests and may not necessarily use the same mobile device.

FIGS. 4A-4B illustrates exemplary embodiments of an aptamer molecular beacon testing device directly fixed to a mobile device. As such, the testing device fixture 29 may be attached to the mobile device 39 with a clamp 53. The fixture 29 may be further attached to the mobile device 39 through a specifically purposed case (e.g. phone case, tablet case, etc.). In order to retain the smallest form factor possible, the test vial slot of the fixture 29 may not necessarily be aligned with the flash 33 and the camera 37 of the mobile device 39. As such, a sample vial 31 inserted in the test vial slot may be aligned with the camera 37 and the camera aperture 37' only. In such embodiments, the fixture 29 may include a mirror 55 to redirect the light source from the flash 33, through the flash aperture 33', towards the sample vial 31. As further described herein, the fixture 29 may include a filter 35 between the sample vial 31 and the camera 37. Additional optics to capture more light from the vial may be added to the system without departing from the teachings of this disclosure. As such, the system may include mirrors, lenses, filter for the light source and any other optical device that may improve or change some optical characteristics inside the enclosure, the test vial or other structure of the test system as described herein.

To prevent any ambient light from degrading the test results, the fixture 29 may further include an opaque seal 41 between the fixture 29 and the mobile device 39, the seal effectively surrounding the apertures for the camera(s) 37' and the flash 33'.

Figure 4C:
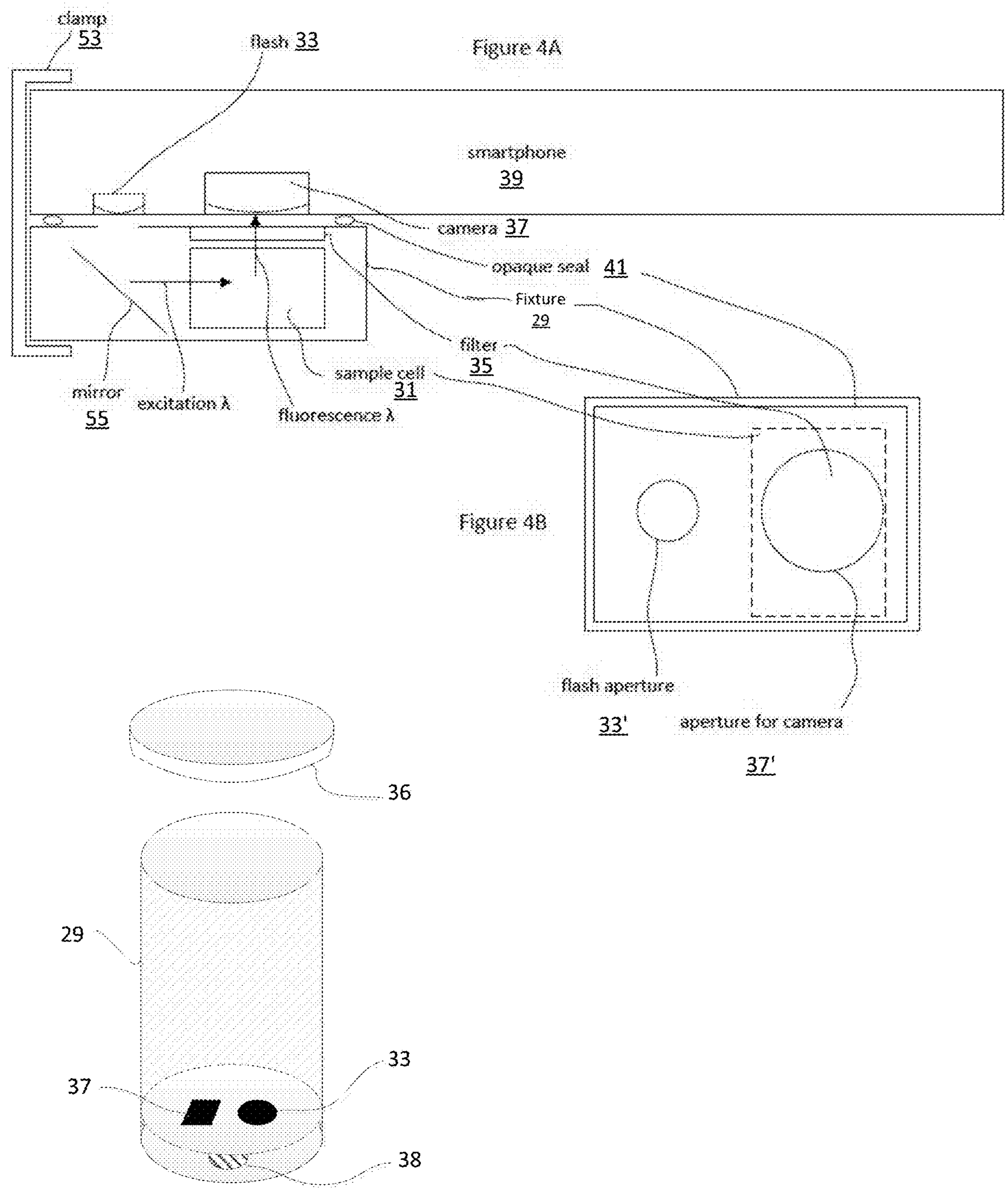
FIG. 4C is a schematic drawing of an exemplary standalone aptamer molecular beacon testing device which includes a light source, a camera module and a communications module.

FIG. 4C is a schematic drawing of an exemplary standalone aptamer molecular beacon testing device which includes a light source 33, a camera cell 37 and a communications module 38. While the aptamer testing device described herein may typically use a mobile device as an efficient device that includes numerous of the systems required for the test, such as a light source, a camera, a processing and calculations mean, the aptamer testing device may equivalently function without a mobile device if the testing device fixture 29 includes all necessary system components.

As illustrated in the embodiment of FIG. 4C, the fixture 29 may be an opaque cylindrical container with sufficient place inside the container to insert a test vial. As such, it will be understood that the shape of the fixture 29 may take any necessary form to accommodate a test vial. A fixture removable cap 36 may be fixed and remove from the fixture 29 to allow access to the container in order to add/remove a test vial. The fixture 29 may include, on a surface to which the content of a test vial would be exposed to, a light source 33 and a camera cell 37. The light source 33 may be a light emitting diode similar to the ones found in mobile device's flash. The camera cell 37 may be specifically sensitive to the wavelength emitted by the fluorophore used in the aptamer contained in a test vial to be used inside such device. The light source 33 and camera cell 37 may have all necessary components to function and be controlled.

The embodiment of FIG. 4C may further include a communications module 38 that may establish a wireless connection to any computing device (e.g. mobile device, computer, etc.). The communications module 38 may use WiFi protocols, Bluetooth protocols or any other protocols allowing exchange of data packets between the testing device and a computing device. In some embodiments, the communications module 38 may include a port such as to allow a wired communication to a computing device. In some embodiments, the communications module 38 may allow a software application running on the connected computing device to control the operation of the light source 33 and of the camera cell 37. As such, the computing device may trigger the light source 33 for a given time and thereafter trigger the capture of the image of the test vial to detect any light emissions from the fluorophores.

Someone skilled in the art will appreciate that other means of triggering the different testing sequence may be used. For example, a test button may be included on the fixture 29 or on the fixture removable cap 36 to trigger the test. The captured image may be automatically transferred to a paired computing device to which the communication module 38 is connected to. The captured image may further be recorded on an on-board non-transitory memory unit, which may allow for subsequent transfer to a computing device.

The fixture 29 may further include a power source to provide sufficient power for the operation of the light source 33, the camera 37 and the communications module 38. For example, the power source may be a rechargeable battery, which may be recharged by connecting a power cable to a port included on the fixture 29. In some embodiments, the battery may be a replaceable battery in a compartment easily accessed.

Although described as communicating with a computing device to process the captured image data and assess the infection state of the tested person, it will be appreciated that the standalone testing device as presented in FIG. 4C may further include necessary electronic components (e.g. microprocessor, memory (transitory and non-transitory), etc.) to internally process all data and provide the infection state feedback without relying on a connected computing device. For example, the testing device may process the captured image data and light a green light or a red light depending on the determined infection state of the tested patient.

It will be further appreciated that any additional optics elements (i.e. filters, mirrors, lenses, etc.) may be added inside the fixture 29 or to the test vial to increase or change certain optical characteristics of the testing device and improve its efficiency at determining the infection state of a tested subject.

Figure 5A:
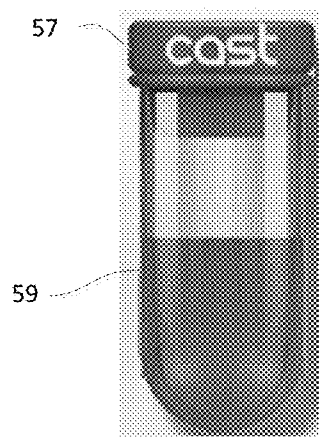
FIGS. 5A-5E are illustrations of exemplary aptamer molecular beacon test vials.

Now referring to FIGS. 5A-5D, which are illustrations of exemplary aptamer molecular beacon test vials. AMB testing vials may have any shape that can fit inside a testing device's test vial slot. As described herein, the testing vial may contain a mix of AMBs and carrier liquid medium and may be opened to add the tested person sample fluid (e.g. saliva, nasal mucus, etc.). FIG. 5A illustrates an embodiment in which a bullet-shaped vial has a container 59 and a cap 57. The vial cap 57 may be twisted or pulled to be removed from the container 59, such that a sample fluid may be added to the mix contained in the container 59. The container 59 may be transparent such as to allow light to pass-through.

Figure 5B:
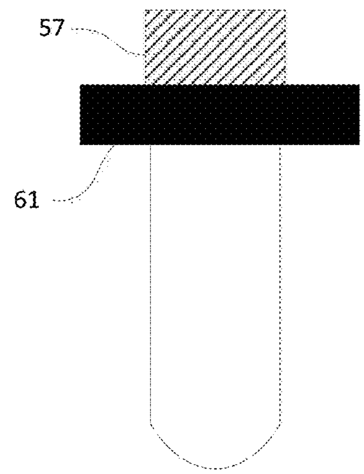

FIG. 5B illustrates an embodiment of a test vial in which the cap 57 includes an opaque seal 61. The opaque seal 61 may fit around the testing device's test vial slot, such that no light may leak through the opening to degrade the test results. Part of the cap 57 may extent upwards from the opaque seal 61 such that it may be manually inserted and removed from the testing device.

Figure 5C:
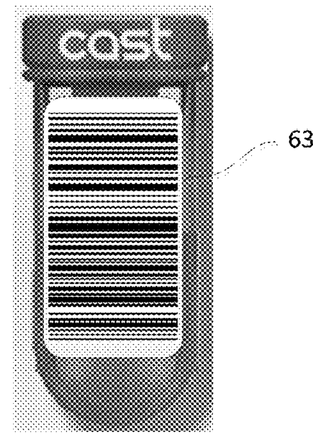

FIG. 5C shows an embodiment in which part of the test vial's container 59 is covered by a barcode sticker 63. The barcode sticker 63 may be scanned by the mobile device being used for the testing and may ensure that the testing vial used is an official vial for the target pathogen being tested (i.e. quality control, it contains the relevant AMBs and in sufficient quantity, etc.). It may also be particularly useful to scan a barcode to ensure that a test vial is not re-used by the person performing the test. Additionally, the barcode sticker 63 may have a reflective underlayer, such that when the test vial is positioned with the barcode sticker 63 facing away from the mobile device, the light may be reflected by its reflective underlayer. This may increase the sensitivity of the test and may replace the addition of a mirror inside the fixture.

In other embodiments, the barcode sticker 63 may be on the cap 57 or may be on a package containing one or more test vials. In yet another embodiment, the barcode sticker 63 may be replaced by any other means of confirming the source of the test vial, such as an RFID tag. In some embodiments, the sticker may strictly be a reflective sticker added to increase the sensitivity of the test.

Figure 5D:
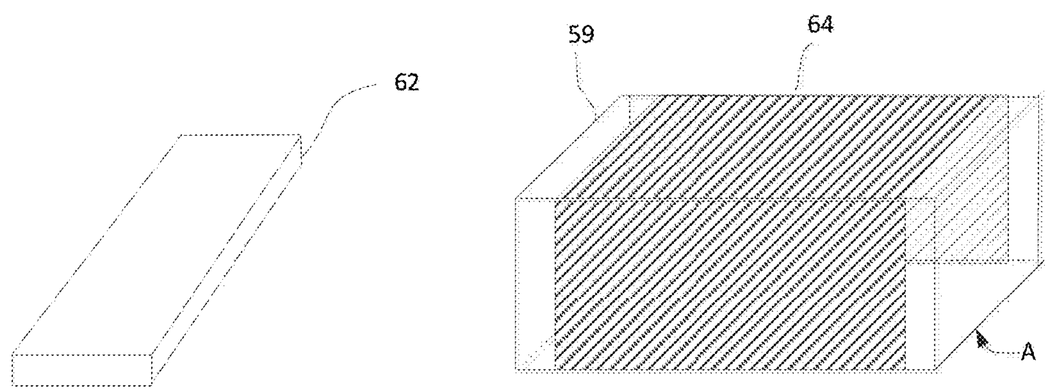

FIG. 5D illustrates a different type of test sample support. The test vial may thus be replaced by a testing slide or substrate 62 over which the mix of AMBs, carrier liquid medium and fluid from the tested subject may be spread. Someone skilled in the art will appreciate that any other shape may be used as a test "vial" and that the term "vial" should not be interpreted as limiting the scope of the present disclosure to a container-type test sample.

Figure 5E:
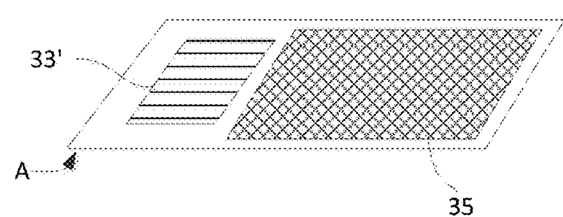

The embodiment illustrated in FIG. 5E may be used without any fixture 29 as a testing device. As such, the vial's container 59, which may be generally of rectangular shape, may include the necessary structures to allow the test. For example, the container 59 may have a reflective sticker 64 wrapped around all but one surface and a top of the container. No matter the shape of the vial, the arrangement of a flat side for optically coupling with the mobile device can be desirable. The reflective sticker 64 may thus prevent ambient light from passing through the sticker 64 into the container. The removable cap may be made out of opaque material such that, once placed on top of the vial's container 59, it may overlap with the sticker 64 to further prevent ambient light leaking inside the container 59. In some embodiments, the reflective sticker 64 may cover a bottom section (i.e. opposite of the cap) of the container 59. In other embodiments, the bottom section of the container 59 may have a bottom cap opaque structure that may provide easier hold of the vial when performing a test.

In the embodiment of FIG. 5E, one side (A) of the vial's container 59 may be configured to be directly pressed against the mobile device's flash and camera structure. As such, this side (A) may include a pass-through area 33' for the flash light source to go through the surface into the content of the container. Additionally, there may be a filtered area with a bandpass optical filter 35 that may be placed over the camera(s) of a mobile device during a test.

Figure 6:
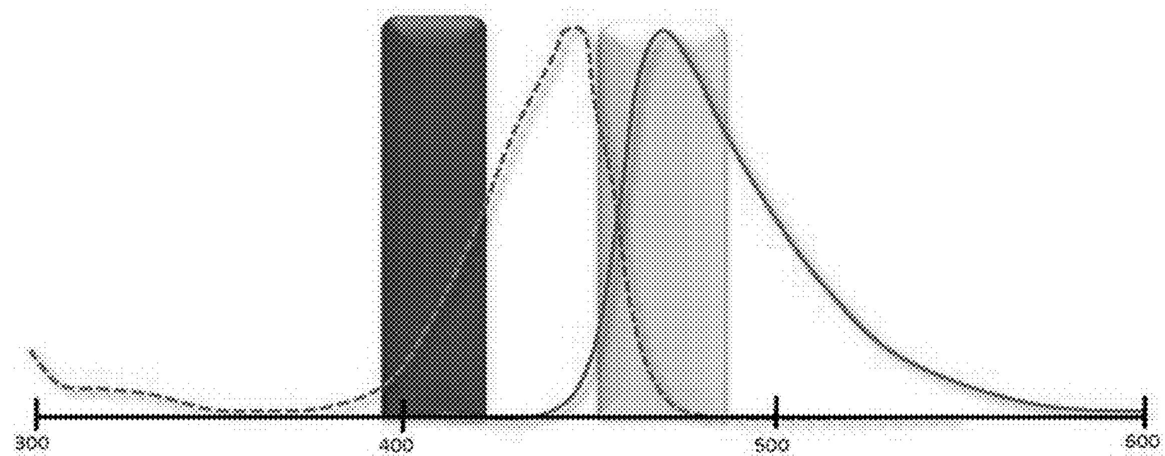
FIG. 6 is a graph of an exemplary fluorescent emission response to a mobile device flash by an Aptamer Molecular Beacon.

FIG. 6 is a graph of an exemplary fluorescent emission response to a mobile device flash by an Aptamer Molecular Beacon. In this embodiment, the light exciting the AMB's reporters may be around 450 nm (dotted line) and the fluorescent response produced by the AMB's reporters may be emitted at a higher wavelength.

Someone skilled in the art will appreciate that specific wavelengths disclosed herein may change with different models of mobile devices, as may the sensitivity of the method and characteristics of the fixture. As a result of such, the Aptamer Molecular Beam specifications (e.g. fluorophore and quencher used, etc.) may also change. However, whether any or all of these changes are made to the aptamer molecular beacon testing device, the underlying principles are the same as taught herein.

Software Application

To operate the aptamer molecular beacon testing device with a mobile device, a software application is required. As a matter of fact, the software application is required as the test requires control over the flash, the camera, computing power and other modules of the mobile device.

Figure 7:
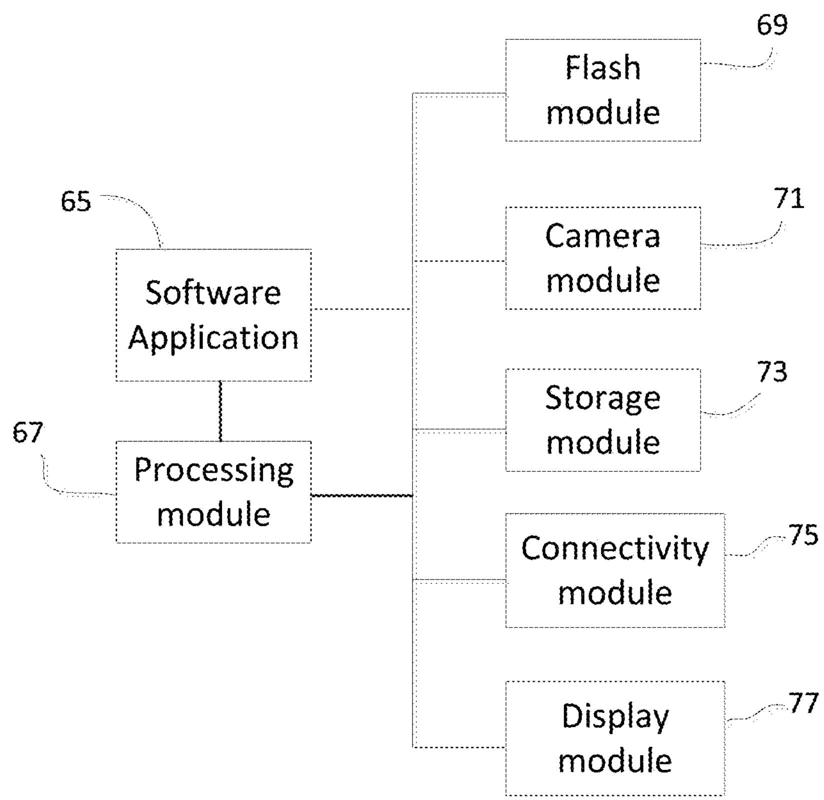
FIG. 7 is a diagram of the modules of an exemplary mobile device running an aptamer molecular beacon test.

Now referring to FIG. 7, which is a diagram of the modules of an exemplary mobile device running an aptamer molecular beacon test. In a mobile device, the software application 65 may have access to numerous modules (herein defined as all the software and hardware components of the mobile device required to control its associated feature). As such, the software application 65 for the aptamer molecular beacon test may access and operate the processing module 67, the flash module 69, the camera module 71, the storage module 73, the connectivity module 75 and the display module 77.

The connectivity module can establish a connection to a server associated with the provider of the test vials. The application 65 can be configured to perform a test only when the user of the application 65 enters a valid code associated with the test vials, such as by acquiring an image of a barcode or by entering a code found on the vial or its packaging. The code can be validated locally by the application 65 using conventional decryption, hash value or checksum verification, or it can be validated by the server. If the code is invalid, the test vial should not be trusted. If ever a batch of vials were to be found to be defective, the server can report to the application 65 that the vial, even with a valid code, is defective and notify the user to seek a replacement using the display module 77.

The software application 65 may thus provide the processing module 67 (which may include the mobile device's processor, transitory and non-transitory memory units, etc.) with instructions which, when they are executed are operable to control the other modules of the mobile device. As such, the flash module 69 may be operated by the software application 65 to trigger at a start of a test and to last for a given timeframe. Once the flash has been operated, the software application 65 may allow the camera module 71 to capture images inside the testing device. The software application 65 may choose the camera lens with the highest quantum efficiency, which may be about 75% at 490 nm. The software application 65 may capture the amount of light emitted by the AMBs reporters over a given capture time, which may be a fixed time or as long as the emission lasts. If the photons that are captured are above the threshold specified in the application to eliminate background optical noise in the system, the pathogen has been detected and this can be displayed or, via the communications capabilities of the mobile, transmitted. If the photons captured are below the threshold, the negative results are displayed or communicated, as required.

The smartphone or other mobile device with the ability to induce a response of the AMBs fluorophores can be programmed to capture a single event (e.g. one flash), or a series of events. Such events then can form databases where the results can be deduced by algorithms or AI that is built into the mobile device.

The displaying of the results may be done through the display module 77 which the software application 65 may control to display any desired information. As described, the results may be communicated to any other system (local or through a wired or wireless connection) or online database through the mobile device's connectivity module 75. A copy of the data (test result, recorded pictures, name of the user, timestamp, barcode of the testing vial, etc.) may also be locally registered on the mobile device's storage module 73. Additionally, when no wired or wireless connections are available, the data may be stored locally before being uploaded to an online server once a connection has been established.

Mobile devices may have numerous other sensors which may allow for the registration and reporting of useful data. As such, the results can contain personal information (as configured by the user or mandated by an official health organization), such as name, time, date, and GPS coordinates. This may be particularly helpful in conjunction with pandemic tracking applications. The software application 65 may thus provide an API to connect to such other apps.

Someone skilled in the art will appreciate that the mobile device capabilities required to perform the functions listed herein maybe performed by other computing devices with the same capabilities as described herein.

Aptamer Molecular Beacon Testing Method

As described herein, the aptamer molecular beacon testing device and the software application running on the mobile device may be used to perform testing against a target pathogen. The Aptamer Molecular Beacon may thus be specific to the target pathogen, such that it may attach to it and its reporter may emit a fluorescent response to a light source. The ability to measure the emitted fluorescence by the mobile device's camera(s) provides the means to establish the amount of virus found (viral load) inside a fluid sample from a person and thereafter to establish the strength of the infection (or the lack of infection). A sequence of tests on the same patient over days may further establish the growth and demise of the infection.

Similarly this method of evaluation of the presence of the virus in any method by using the power of a mobile device or similar device can improve the acquired results and eliminate the human factor such as in PCR based tests for virus or other pathogens.

Figure 8:
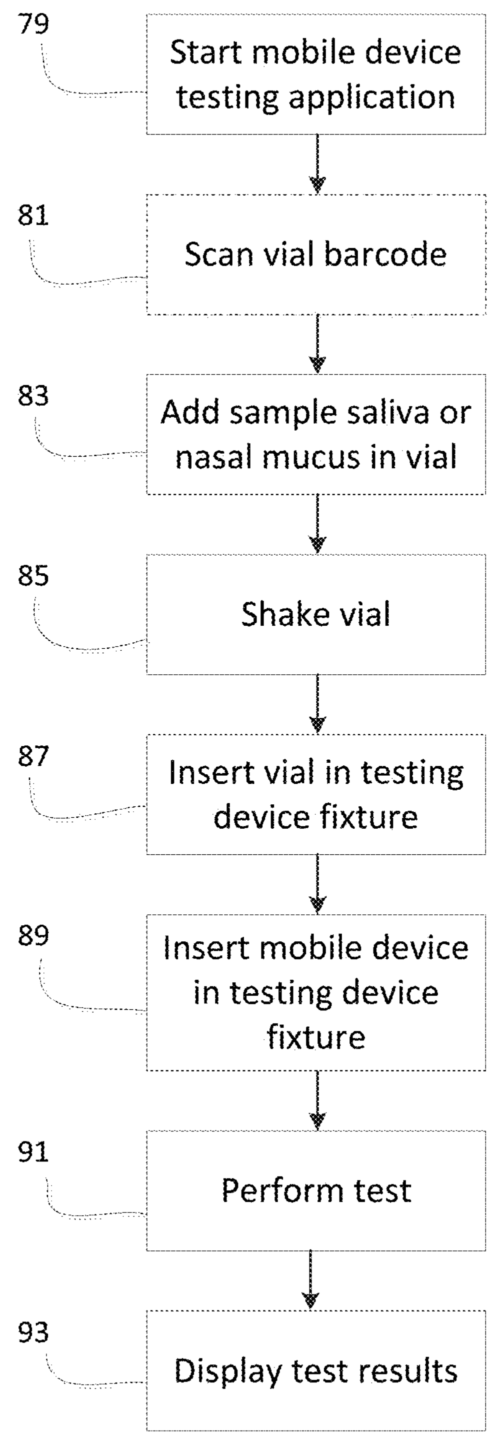
FIG. 8 is a flowchart of an exemplary method of testing for a target pathogen using an aptamer molecular beacon testing device with a mobile device.

Now referring to FIG. 8, which is a flowchart of an exemplary method of testing for a target pathogen using an aptamer molecular beacon testing device with a mobile device. The person performing the test, which may be the test subject or another tester/operator, may start the testing sequence by starting the mobile device's testing application 79. If the test vials are configured with a barcode, the person performing the test may thereafter scan the vial's barcode 81. In some embodiments, this may provide necessary information to the testing software application, such as which pathogen is being tested, the state of the vial (e.g. first-time use, reuse, contaminated batch, etc.) and any other relevant information.

Afterwards, the tested subject may add a sample of fluid, such as saliva or nasal mucus 83 inside the vial containing the AMBs and a carrier liquid medium. In order to properly mix the sample fluid with the AMBs, the vial may then be shaken 85 for a predetermined amount of time. Once completed, the tester may insert the vial inside the testing device's vial slot 87. The mobile device may further be inserted in the testing device's fixture 89 and the test may be subsequently performed 91.

Performing the test 91 may include triggering the flash light source for a given period of time. The image capture may thereafter be done either immediately after the flash light source has extinguished (i.e. when using certain fluorophores, they may continue to emit light for a given time even after the excitation input is removed; this may therefore be used with embodiments of the device which does not include a filter for the camera as the only light that may be captured would come from fluorophores) or may be done while the flash light source is still providing light to the test vial. In some embodiments, the testing device may proceed to a number of flash light source and image capture cycles, such as to have multiple data points that may be used in the image post-processing step.

Once the test has been completed and the software application has run its analysis of the captured images, the test results may be displayed 93 on the mobile device. In some embodiments, the test results may be further communicated and/or stored locally or on a remote server.

It will be recognized that this method of detecting virus and other pathogens, forming light emitting molecular beacons formed from aptamers with fluorophores matched to the flash spectrum of the flash light and spectral sensitivity of the cameras, is a new and efficient means of detecting any type of virus, or parts thereof, or surface proteins, that binds to the specifically tailored sequences of the probe that is an aptamer or other biological molecular sequence. While aptamers with fluorophore reporters have been described in prior art research, its uses have generally been limited to detection by spectroscopy or using specialized tools and devices. Being able to test and detect a response from a simple mobile device, as a vast majority of the worldwide population have access to, is a significant improvement.

What is claimed is:

1. A method for detecting a pathogen comprising:

adding a test subject sample fluid to a replaceable aptamer molecular beacon test vial comprising a solution of Aptamer Molecular Beacons and a carrier liquid medium, wherein said Aptamer Molecular Beacons are selected to bind to a protein, RNA or DNA of a target pathogen and further comprise a reporter molecule and a quencher molecule, said reporter molecule being operable to receive light and emit light after binding to said target pathogen, said binding modifying a configuration of said Aptamer Molecular Beacons from a quenched configuration, where said quencher molecule is in proximity with said reporter molecule, to an emitting configuration where said quencher molecule and said reporter molecule are separated;

mixing a content of said replaceable aptamer molecular beacon test vial;

aligning said aptamer molecular beacon test vial with a camera and a flash light source of a mobile computing device, wherein said aligning comprises inserting said mobile computing device into a slot in a light proof enclosure;

using a software testing application on said mobile computing device to perform a test to detect a presence of said target pathogen by operating said flash light to illuminate said solution in said vial to excite said reporter molecule and acquiring at least one image of emission from said reporter molecule using said camera; and using said software testing application on said mobile computing device for at least one of computing an infection status based on said captured image and displaying said infection status on a display of said mobile computing device.

2. The method as defined in claim 1, further comprising storing at least one of said captured image and said infection status in a storage module of said mobile device.

3. The method as defined in claim 2, further comprising sending at least one of said captured image and said infection status to a remote server.

4. The method as defined in claim 1, further comprising one of receiving a user input code on said mobile computing device and scanning a barcode associated with said vial using said camera of said mobile computing device to determine at least one of the state of said replaceable test vial and a target pathogen being tested.

5. The method as defined in claim 4, further comprising using said software testing application on said mobile computing device to communicate with a remote server to validate said replaceable test vial based on one of said code and said barcode.

6. The method as defined in claim 5, further comprising preventing said mobile device from being operable to determine infection status when the state of the replaceable test vial indicates an invalid replaceable test vial.

7. The method as defined in claim 4, further comprising preventing said mobile device from being operable to determine infection status when the state of the replaceable test vial indicates an invalid replaceable test vial.

8. The method as defined in claim 1, further comprising using said software testing application on said mobile computing device to analyze said image to confirm a presence of said replaceable test vial, wherein a negative infection status test result can be prevented.

9. The method as defined in claim 8, further comprising providing a reference element to be imaged with said vial, wherein said presence is confirmed by processing said captured image to identify said reference element.

10. The method as defined in claim 1, further comprising placing a bandpass optical filter over said camera so as to have sensitivity to emission from said reporter molecule.

11. The method as defined in claim 1, wherein said vial is adapted to have apertures for said flash light source and said camera and to provide protection from ambient light.

12. The method as defined in claim 1, wherein said acquiring comprises acquiring an image immediately following operating said flash light to illuminate said solution in said vial to excite said reporter molecule.

13. The method as defined in claim 1, wherein said at least one image of emission from said reporter molecule using said camera is analyzed to determine a severity of an infection or disease.

* * * * *